United States Patent
Radford et al.

(10) Patent No.: US 10,578,612 B2
(45) Date of Patent: Mar. 3, 2020

(54) DIAGNOSTIC ASSAY

(75) Inventors: Anthony J. Radford, Southbank (AU); Emily Manktelow, Kangaroo Ground (AU); Jeff Boyle, Pearcedale (AU); Jenny Louise Howard, Bentleigh East (AU)

(73) Assignee: Cellestis International Pty Ltd., Chadstone (AU)

( * ) Notice: Subject to any disclaimer, the term of this patent is extended or adjusted under 35 U.S.C. 154(b) by 514 days.

(21) Appl. No.: 13/700,720

(22) PCT Filed: May 23, 2011

(86) PCT No.: PCT/AU2011/000608
§ 371 (c)(1),
(2), (4) Date: Jul. 16, 2013

(87) PCT Pub. No.: WO2011/146968
PCT Pub. Date: Dec. 1, 2011

(65) Prior Publication Data
US 2013/0289139 A1 Oct. 31, 2013

Related U.S. Application Data

(60) Provisional application No. 61/349,801, filed on May 28, 2010.

(51) Int. Cl.
*C12N 5/071* (2010.01)
*G01N 33/53* (2006.01)
*G01N 33/543* (2006.01)
*G01N 33/50* (2006.01)

(52) U.S. Cl.
CPC ....... *G01N 33/543* (2013.01); *G01N 33/5047* (2013.01)

(58) Field of Classification Search
None
See application file for complete search history.

(56) References Cited

U.S. PATENT DOCUMENTS

| | | | |
|---|---|---|---|
| 4,016,043 A | 4/1977 | Schuurs et al. | |
| 4,018,653 A | 4/1977 | Mennen | |
| 4,424,279 A | 1/1984 | Bohn et al. | |
| 5,334,504 A * | 8/1994 | Wood | G01N 33/6866 435/7.32 |
| 6,719,973 B1 | 4/2004 | Ding et al. | |
| 2001/0006789 A1* | 7/2001 | Maino | G01N 33/56972 435/7.21 |

OTHER PUBLICATIONS

Khan et al., 2008, Clin. Vacc. Immunol. vol. 15: 974-980.*
Guillot et al., 2005, J. Biol. Chem. vol. 280: 5571-80.*
Giuliani et al.,2010, Methods in Mol. Biol. vol. 618: 137-154.*
Manetti et al., 1995, Eurk. J. Immunol. vol. 25: 2656-2660.*
Balboni et al., 2006, Annu. Rev. Immunol. vol. 24: 391-418.*
Bouteiller et al., 2005, JBC pp. 1-24.*
Lamping et al., 1996, J. Immunol. vol. 157: 4648-4656.*
Orinska et al., 2005, Blood. vol. 106: 978-987.*
Hamann et al., 2005, Infect. Immun. vol. 73: 193-200.*
Tabiasco et al., 2006, J. Immunol. vol. 177: 8708-8713.*
Segura et al., 2006, FEMS Immunol. Micro. vol. 47: 92-106.*
Zheng et al., 2012, Vet. Micro. vol. 156: 147-156.*
Ye et al., Jan. 2009, JID, vol. 199: 97-107.*
Bigos et al., "Nine Color Eleven Parameter Immunophenotyping Using Three Laser Flow Cytometry," *Cytometry* 36:36-45, 1999.
Blanchard-Rohner et al., "Comparison of a limiting dilution assay and ELISpot for detection of memory B-cells before and after immunisation with a protein-polysaccharide conjugate vaccine in children," *Journal of Immunological Methods* 358:46-55, 2010.
Cardoso et al., "Polymyxin B as inhibitor of LPS contamination of Schistosoma mansoni recombinant proteins in human cytokine analysis," *Microbial Cell Factories* 6(1):2007, pp. 1-6.
Daneshvar et al. "Detection of biomolecules in the near-infrared spectral region via a fiber optic immunosensor," *Journal of Immunological Methods* 226:119-128, 1999.
Ding et al., "The Sushi peptides: structural characterization and mode of action against Gram-negative bacteria," *Cellular and Molecular Life Sciences* 65:1202-1219, 2008.
Duff et al., "The Inhibitory Effect of Polymyxin B on Endotoxin-Induced Endogenous Pyrogen Production," *Journal of Immunological Methods* 52:333-340, 1982.
Durig et al., "Fourier Transform Raman Spectroscopy of Brightly Colored Commercially Available Dyestuffs and Pigments," *Journal of Raman Spectroscopy* 24:281-285, 1993.
Eiwegger et al., "Allergen specific responses in cord and adult blood are differentially modulated in the presence of endotoxins," *Clinical and Experimental Allergy* 28:1627-1634, 2008.
Eriksson et al. "Lipid and water diffusion in bicontinuous cubic phases measured by NMR," *Biophysical Journal* 64:129-136, Jan. 1993.
Fu et al., "A microfabricated fluorescence-activated cell sorter," *Nature Biotechnology* 17:1109-1111, Nov. 1999.
Jeong et al., "Blocking of monocyte-associated B7-H1 (CD274) enhances HCV-specific T cell immunity in chronic hepatitis C infection," *Journal of Leukocyte Biology* 83:755-764, 2008.
Jin et al., "Induction of potent cellular immune response in mice by hepatitis C virus NS3 protein with double-stranded RNA," *Immunology* 122:15-27, 2007.
Lakowicz et al., "Time-Resolved Fluorescence Spectroscopy and Imaging of DNA Labeled with DAPI and Hoechst 33342 Using Three-Photon Excitation," *Biophysical Journal* 72:567-578, Feb. 1997.
Lawn et al., "Utility of interferon-γ ELISPOT assay responses in highly tuberculosis-exposed patients with advanced HIV infection in South Africa," *BMC Infectious Diseases* 7:99, 2007, 9 pages.

(Continued)

*Primary Examiner* — Amy E Juedes
(74) *Attorney, Agent, or Firm* — Seed IP Law Group LLP

(57) ABSTRACT

The present disclosure relates generally to the field of immunological-based diagnostic assays. Particularly, a method is contemplated herein for measuring cell-mediated immune response reactivity. The present disclosure further provides a method to reduce incidence of non-specific immune response reactivity in a cell-mediated immune response-based assay, comprising contacting a sample with a basic peptide structure capable of binding to lipopolysaccharides, such as polymyxin B or a sushi peptide.

9 Claims, 2 Drawing Sheets
Specification includes a Sequence Listing.

(56) References Cited

OTHER PUBLICATIONS

Lewis et al., "Erratum to "The use of Fourier Transform Infrared (FT-IR) spectroscopy to study the state of heterobifunctional reactive dyes"," *Dyes and Pigments* 42:197, 1999.

Rahman et al., "Infrared and Raman Spectra of a Single Resin Bead for Analysis of Solid-Phase Reactions and Use in Encoding Combinatorial Libraries," *The Journal of Organic Chemistry* 63: 6196-6199, 1998.

Rapaport et al., "Visible light emission from dyes excited by simultaneous absorption of two different frequency beams of light," *Applied Physics Letters* 74(3):329-331, Jan. 18, 1999.

Ribas et al., "Standardization of MHC Tetramer and ELISPOT Assays to Quantitate Antigen-Specific T Cell Expansion after CTLA4 Blockade," *Journal of Immunotherapy* 27(6):S43, 2004.

Tawa et al., "Polarized Light-Induced Anisotropy in Polymer Films Doped with Az Dyes in the Photostationary State Studied by IR Spectroscopy," *Materials Research Society Symposium Proceedings* 488:885-890, 1998.

Van der Kleij et al., "Responses to Toll-Like Receptor Ligands in Children Living in Areas Where Schistosome Infections Are Endemic," *The Journal of Infectious Diseases* 189:1044-1051, 2004.

Venken et al., "A Cfse based assay for measuring CD4, CD25, regulatory T cell mediated suppression of auto-antigen specific and polyclonal T cell responses," *Journal of Immunological Methods* 322:1-11, 2007.

Youvan et al., "Calibration of Fluorescence Resonance Energy Transfer in Microscopy Using Genetically Engineered GFP Derivatives on Nickel Chelating Beads," *Biotechnology* 3:1-18, 1997.

Zhang et al., "Specific suppression in regulatory T cells by Foxp3 siRNA contributes to enhance the in vitro anti-tumor immune response in hepatocellular carcinoma patients," *Journal of Peking University* (*Health Science*) 41(3):313-317, 2009.

Zhong et al., "Induction of cytolytic activity and interferon-γ production in murine natural killer cells by polymyxins B and E," *International Immunopharmacology* 8:508-513, 2008.

* cited by examiner

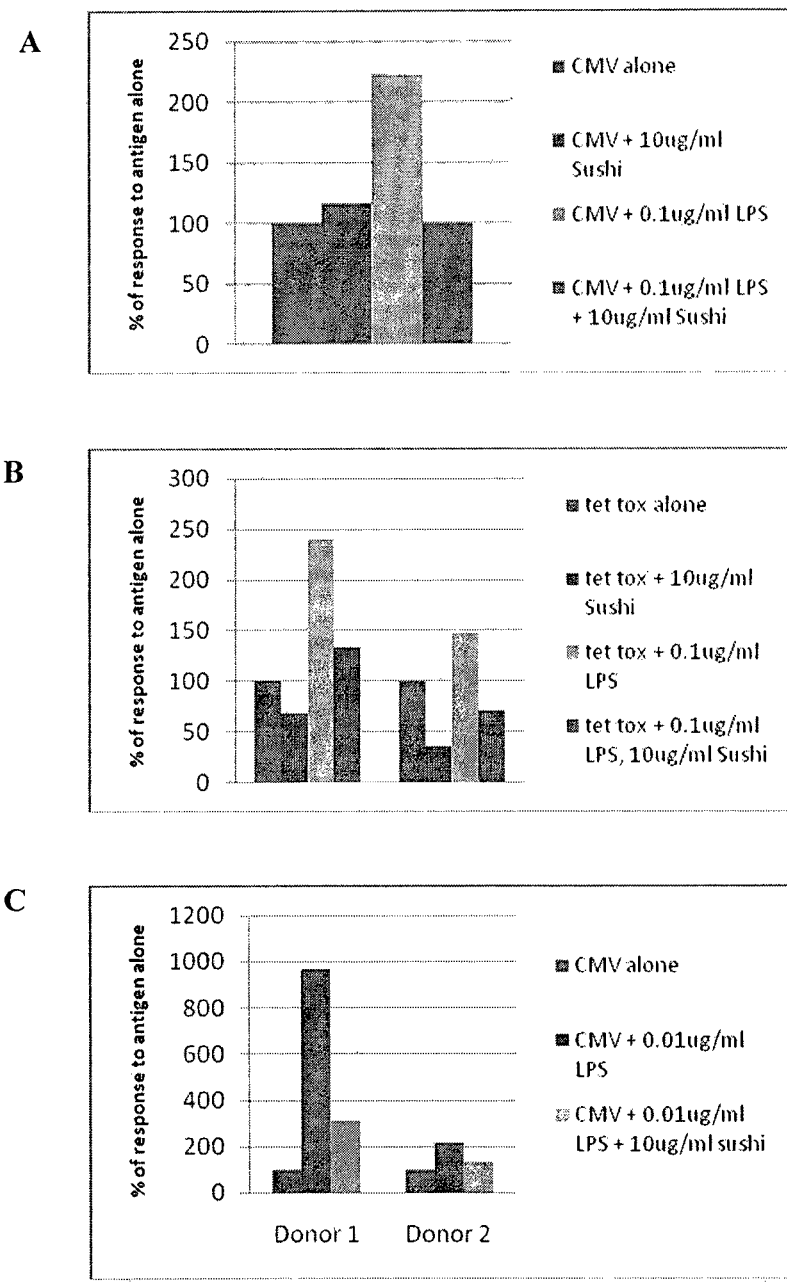
Figures 2a, b and c

```
SEQUENCE LISTING

<160> NUMBER OF SEQ ID NOS: 1

<210> SEQ ID NO 1
<211> LENGTH: 34
<212> TYPE: PRT
<213> ORGANISM: artificial sequence
<220> FEATURE:
<223> OTHER INFORMATION: Sushi peptide

<400> SEQUENCE: 1

His Ala Glu His Lys Val Lys Ile Gly Val Glu Gln Lys Tyr Gly Gln
1               5                   10                  15

Phe Pro Gln Gly Thr Glu Val Thr Tyr Thr Cys Ser Gly Asn Tyr Phe
            20                  25                  30

Leu Met
```

DIAGNOSTIC ASSAY

This application is associated with and claims priority from U.S. Provisional Patent Application No. 61/349,801, filed on 28 May 2010, entitled "A diagnostic assay", the entire contents of which, are incorporated herein by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200185_403USPC_SEQUENCE LISTING.txt. The text file is 814 bytes, was created on Feb. 14, 2013, and is being submitted electronically via EFS-Web.

FIELD

The present disclosure relates generally to the field of immunological-based diagnostic assays. Particularly, a method is contemplated herein for measuring cell-mediated immune response reactivity. The present disclosure further provides a cell-mediated immune response-based assay to detect or monitor a disease or condition with a reduced incidence of non-specific immune response reactivity.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Immunological-based diagnostics provides an important tool in detecting a variety of disease conditions. This is especially the case given the specificity of components within the immune system. Notwithstanding, diagnostic outcomes can be compromised when there is non-specific immune reactivity. This can lead to false positives and potentially mis-diagnoses. There is a need to develop diagnostic assays with enhanced specificity.

One form of immunological-based diagnostic assay involves the stimulation of T-cells with antigens or mitogens in either isolated cell culture or in whole blood culture followed by the detection of effector molecules such as cytokines produced by the activated T-cells (also referred to as effector T-cells). The effector molecules are generally detected using techniques such as enzyme immunoassays, multiplex bead analysis, ELISpot and flow cytometry. Such assays are useful for detecting disease-specific T-cell responses.

In an embodiment of the above-mentioned assay, a T-cell response is measured using whole blood. Such assays are useful in the diagnosis of tuberculosis infection. However, an impediment to these types of assays is the non-specific production of effector molecules such as occurring when there is contamination by immune stimulants such as endotoxins. This is particularly the case in blood collection tubes which may be a source of endotoxin contamination. Endotoxins may also be in a blood sample itself. Such immune stimulant contaminants can lead to false positive results and potential mis-diagnoses.

An improved immune cell-mediated based assay is, therefore, needed. In particular, such assays are useful in detecting or monitoring a range of diseases and conditions in a subject with enhanced specificity.

SUMMARY

Taught herein is a method for detecting cell-mediated immune response activity via enhanced effector molecule production, i.e., with a reduced risk or incidence of non-specific effector molecule production such as caused by immune stimulant contaminants including endotoxins. Whilst cell isolation and depletion steps may also be undertaken, the assay of the present disclosure can be conducted using whole blood without need for laborious cell isolation or depletion steps. The assay enabled herein exhibits enhanced specificity. Hence, the risk of false positives and, therefore, mis-diagnoses are reduced. This is important where immune stimulant contaminants such as endotoxins occur in blood collection tubes, or in blood itself or in other components used in the assay or during blood collection. In another embodiment, the antigen-specific response is further enhanced using an immune response stimulant. Examples of immune response stimulants include synthetic or naturally occurring nucleic acid molecules such as but not limited to a synthetic double-stranded RNA. One synthetic RNA herein is polyinosinic acid-polycytidylic acid (poly(I:C)) or its functional equivalent.

In an embodiment, the immune cells are contacted with an antigen associated with a disease condition to be assessed following or simultaneously with a basic peptide structure capable of binding to cell lipopolysaccharides or a chemical analog thereof or its functional equivalent. Such a basic peptide may also be described as a cationic detergent-like antibiotic. The method enabled herein is useful in detecting or monitoring a disease or condition including the level or stage of the disease or condition in a subject such as an infection by a pathogenic agent, an autoimmune disease, cancer and an inflammatory condition with enhanced specificity. Other conditions include exposure to toxic agents such as beryllium. In an embodiment, the basic peptide structure capable of binding to cell lipopolysaccharides is a member of the polymyxin B family of antibiotics such as polymyxin B itself or a chemical analog thereof or its functional equivalent. In another embodiment, the basic peptide is a member of the sushi peptide family such as the sushi peptide having the amino acid sequence set forth in SEQ ID NO:1, or a chemical analog or functional equivalent thereof. In a further embodiment, an immune response stimulant is also employed such as a synthetic or naturally occurring double-stranded nucleic acid molecule. In an embodiment, the synthetic or naturally occurring nucleic acid molecule is high molecular weight poly(I:C) or its functional equivalent.

Accordingly, an aspect taught herein contemplates a method for measuring cell-mediated immune response activity in a subject, the method comprising contacting a source of immune cells from the subject with an antigen to which the cell-mediated immune response is to be tested in the presence of a basic peptide structure capable of binding to cell lipopolysaccharides and measuring the presence or elevation in the level of an immune effector molecule from the immune cells wherein the presence or level of the immune effector molecule is indicative of the level of cell-mediated responsiveness of the subject.

The immune response may be an antigen-specific immune response or an innate immune response. In relation to the former, the immune cells would include T-cells.

Another aspect taught herein provides a method for measuring cell-mediated immune response activity in a subject, the method comprising contacting a source of immune cells from the subject with an antigen to which the cell-mediated immune response is to be tested in the presence of a basic peptide structure capable of binding to cell lipopolysaccharides and measuring the presence or elevation in the level of an immune effector molecule from the immune cells wherein the presence or level of the immune effector molecule is indicative, of the level of cell-mediated responsiveness of the subject wherein the level of responsiveness is indicative of the presence or absence or level or stage of a disease or condition selected from the list comprising an infection by a pathogenic agent, an autoimmune disease, a cancer, an inflammatory condition and exposure to a toxic agent.

Still another aspect enabled herein contemplates an assay to detect the presence, absence, level or stage of a disease or condition in a subject, the method comprising contacting a source of immune cells from the subject with an antigen to which a cell-mediated immune response is to be tested in the presence of a basic peptide structure capable of binding to cell lipopolysaccharides and measuring the presence or elevation in the level of an immune effector molecule from the immune cells wherein the presence or level of the immune effector molecule is indicative of the disease or condition.

Even yet another aspect taught herein provides a method for measuring cell-mediated immune response activity in a subject in the presence of potential immune stimulant contaminants such as an endotoxin, the method comprising contacting a source of immune cells from the subject with an antigen to which the cell-mediated immune response is to be tested in the presence of a basic peptide structure capable of binding to cell lipopolysaccharides and measuring the presence or elevation in the level of an immune effector molecule from the immune cells wherein the presence or level of the immune effector molecule is indicative of the level of cell-mediated responsiveness of the subject.

Hence, the method enabled by the present specification can be conducted in the presence of a potential immune stimulant contaminant such as an endotoxin with substantially no or little non-specific immune stimulation.

In an embodiment, the basic peptide structure capable of binding to cell lipopolysaccharides is a member of the polymyxin B family of antibiotics such as polymyxin B itself or a chemical analog or functional equivalent thereof. In another embodiment, the basic peptide is a sushi peptide or a chemical analog or functional equivalent thereof. The immune stimulant contaminant includes an endotoxin in a blood collection tube or in a blood sample itself or in a component used in the assay or present during blood collection or storage. In yet another embodiment, an immune response stimulant is also added such as but not limited to a synthetic nucleic acid molecule such as a high molecular weight poly(I:C).

In a further embodiment, the immune cells are T-cells and the assay comprises contacting the T-cells with an agent which modulates the function or activity of T-cells or a subset thereof such as regulatory T-cells (T-reg cells) as well as a basic peptide structure capable of binding to cell lipopolysaccharides.

The method described herein may also be referred to as an "assay". The assay herein is useful inter alia in assessing the general immune responsiveness of a subject or for detecting the responsiveness to specific disease conditions such as autoimmune disease, Celiac's disease, cancer or infection by a pathogenic organism or agent. The source of immune cells is conveniently whole blood but the present disclosure contemplates the use of any source of immune cells including fractionated samples comprising immune cells as well as samples having undergone cell sub-type isolation and/or depletion. Optionally, a simple sugar such as dextrose or glucose is added to the reaction mixture. Reference to "whole blood" includes whole blood without dilution as well as where whole blood is used in an assay at a volume of from about 10% to about 100% of the total sample assay volume (i.e. reaction mixture).

In a particular embodiment, T-reg cells in a T-cell sample are targeted by an agent for function or activity modification. The modification may be to inhibit T-reg cells which have an immune suppressor function or to augment particular cells which have an immune stimulatory function. Examples of agents include CD25 ligands, CTLA4 ligands, sense or antisense oligonucleotides to particular genes or mRNA encoding molecules such as a Janus Kinase 1 (JAK1) or a Tyrosine Kinase 2 (TYK2) and stimulating agents such as CpG containing oligonucleotides which act via toll-like receptors (TLRs) and/or via other mechanisms. Hence, provided herein is the use of a CD25 ligand, a CTLA4 ligand, an oligonucleotide complementary or homologous to genetic material (RNA or DNA) encoding a JAK1 or TYK2 molecule in combination with a basic peptide structure capable of binding to cell lipopolysaccharides such as polymyxin B or a chemical analog or functional equivalent thereof or a sushi peptide to augment or enhance the specificity of an immune cell-mediated assay. The oligonucleotides contemplated herein may have a modified backbone or have chemically modified nucleotides or nucleosides such as phosphorothioates-modified oligonucleotide.

One type of T-reg cell modulating agent may be used or two or all three types of agents may be employed together with the basic peptide structure capable of binding to cell lipopolysaccharides.

The subject includes a human or non-human animal. Hence, the method herein has human medical, veterinary and livestock applications. Humans represent a particularly useful subject in the practice of the subject method.

Hence, in an embodiment, a method is contemplated herein for detecting the presence, absence, level or stage of a disease or condition in a human subject, the method comprising contacting whole blood, which comprises at least 10% of the total volume in a reaction mixture, with polymyxin B or a sushi peptide or a chemical analog or functional equivalent thereof and optionally an agent which inhibits regulatory T-cell function and an antigen to which a cell-mediated immune response is to be tested and measuring the presence or elevation in the level of an immune effector molecule from T-cells wherein the presence or level of the immune effector molecule is indicative of the disease or condition. Reference to a functional equivalent of polymyxin B includes a basic peptide structure capable of binding to cell lipopolysaccharides.

Another aspect taught herein is a method for detecting the presence, absence, level or stage of a disease or condition in a human subject in the presence of a potential immune stimulant contaminant such as an endotoxin the method comprising contacting whole blood, which comprises at least 10% of the total volume in a reaction mixture, with polymyxin B or a sushi peptide or a chemical analog or functional equivalent thereof and optionally an agent which inhibits regulatory T-cell function and an antigen to which a cell-mediated immune response is to be tested and measuring the presence or elevation in the level of an immune effector molecule from T-cells wherein the presence or level of the immune effector molecule is indicative of the disease or condition.

As indicated above, an immune response stimulant may also be employed such as but not limited to a synthetic nucleic acid molecule. Examples include poly(I:C).

Kits and skin tests also form embodiments of the present method.

In an embodiment, the sample is whole blood which is collected in collection tubes containing the antigen or to which the antigen is added for incubation. Generally, blood is maintained in the presence of heparin. Heparin may be in the tube when blood is added or is added subsequently. The use of blood collection tubes is compatible with standard automated laboratory systems and these are amenable to analysis in large-scale and random access sampling. Blood collection tubes also minimize handling costs and reduces laboratory exposure to whole blood and plasma and, hence, reduces the risk of laboratory personnel from contracting a pathogenic agent such as human immunodeficiency virus (HIV), hepatitis B virus (HBV) or hepatitis C virus (HCV). Furthermore, use of the collection tubes to conduct the incubation renders the assay more sensitive than the previously used 24 well culture well plates. One difficulty is that blood collection tubes may be a source of contamination with endotoxins leading to false positive results. Furthermore, any of the components used in the assay may also be contaminated with an endotoxin again leading to false positives. The present method addresses these potentialities and increases the specificity of the immune reaction.

Enabled herein is an enhanced cell-mediated immune assay comprising in one embodiment the use of a collection tube, optionally a simple sugar such as dextrose and the incubation step with an antigen and a basic peptide structure capable of binding to cell lipopolysaccharides and optionally an agent which modulates T-cell function or activity. The incubation step is generally from about 5 to about 50 hours. The dextrose or other simple sugar is generally in a dried form or even immobilized or dried to the tube. A dried form of the sugar may also be added to the blood sample.

The immune effector molecules are generally a cytokine such as but not limited to IFN-γ or an interleukin (e.g. IL-2, IL-4, IL-6, IL-10, IL-12 or IL13 or transforming growth factor beta [TGFβ] or tumor necrosis factor alpha (TNFα) or a granulocyte or granulocyte macrophage colony stimulating factor [G-CSF and GM-CSF, respectively]). The presence or level of immune effector may be determined at the level of the molecule itself or to the extent to which a gene is expressed encoding the molecule.

The subject assay reduces the risk or incidence of false positives and, hence, mis-diagnoses. False positives can occur in the presence of immune stimulant contaminants such as endotoxins.

BRIEF DESCRIPTION OF THE FIGURES

Some figures contain color representations or entities. Color photographs are available from the Patentee upon request or from an appropriate Patent Office. A fee may be imposed if obtained from a Patent Office.

FIGS. 2a through 2c are graphical representations of the inhibition of an immune response to lipopolysaccharide (LPS) by the addition of sushi peptide (SEQ ID NO:1) [0-10 µg/ml] in the presence of different antigens cytomegalovirus [CMV] and tetanus toxoid).

DETAILED DESCRIPTION

Figure 1:
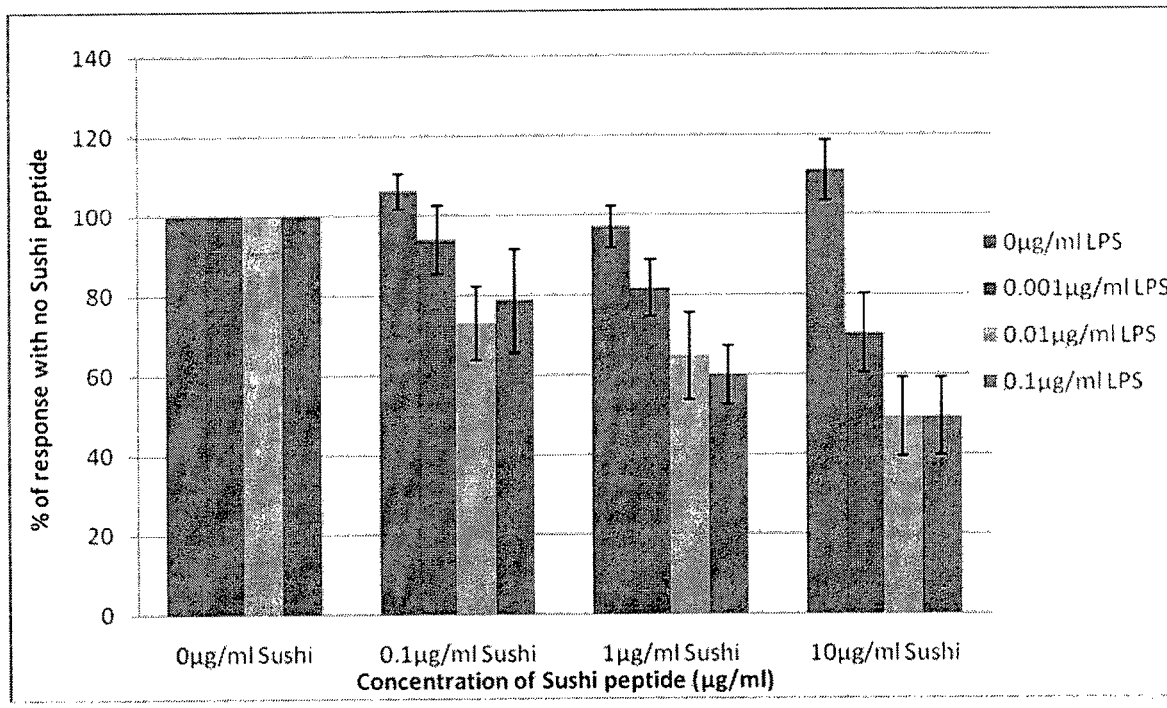
FIG. 1 is a graphical representation of the effects of sushi peptide (SEQ ID NO:1) [0-10 µg/ml] on immune response.

Throughout this specification, unless the context requires otherwise, the word "comprise", or variations such as "comprises" or "comprising", is to understood to imply the inclusion of a stated element or integer or method step or group of elements or integers or method steps but not the exclusion of any other element or integer or method step or group of elements or integers or method steps.

An amino acid sequence is referred to herein by a sequence identifier number (SEQ ID NO). The SEQ ID NO corresponds numerically to the sequence identifier <400>1 (SEQ ID NO:1). A summary of the sequence identifier used herein is provided in Table 1. A sequence listing is provided after the claims.

TABLE 1

| Summary of sequence identifiers | |
|---|---|
| SEQUENCE ID NO: (SEQ ID NO©) | DESCRIPTION |
| 1 | Sushi peptide |

As used in the subject specification, the singular forms "a", "an" and "the" include plural aspects unless the context clearly dictates otherwise. Thus, for example, reference to "a T-cell" includes a single T-cell, as well as two or more T-cells; reference to "an effector molecule" or "an immune cell" includes a single effector molecule or single immune cell, as well as two or more effector molecules or immune cells; reference to "the embodiment" includes single or multiple embodiments; and so on.

Terms such as "agent", "reagent", "compound" and "cell" are used herein to refer to a chemical or biological entity which is involved in the assay for detecting a cell-mediated immune response or the level of such a response.

Reference to an "agent", "reagent", "compound" and "cell" also includes combinations of two or more of such entities. A "combination" also includes multi-part such as a two-part composition where the agents are provided separately and used or dispensed separately or admixed together prior to dispensation. For example, a multi-part assay pack may have two or more agents separately maintained. Hence, this aspect taught herein includes an antigen and a basic peptide structure capable of binding to cell lipopolysaccharides dried and loose or immobilized to a compartment wall or solid support in an assay pack. In another embodiment, the collection tubes may contain a simple sugar in dried form to which reagents are added. Alternatively, a dried form of the simple sugar is added to the tube or to a blood sample. In yet another embodiment, the collection tube comprises a synthetic or naturally occurring double-stranded RNA such as poly(I:C) or its functional equivalent.

Taught herein is the enhanced specificity of effector molecule production from stimulated immune cells such as T-cells or NK cells or other cells of the induced or innate immune system. The enhanced specificity includes reduced incidence or risk of non-specific effector molecule production such as caused by contamination by immune stimulants such as endotoxins. This is particularly important when blood collection tubes or blood itself contain such stimulants or contaminants are part of components added during the assay or when blood is collected or stored. This allows for fewer false positives in the assessment of the cell mediated immune responsiveness of a subject. Enabled herein is an assay to detect, assess or otherwise monitor a cell-mediated response in a subject by measuring the presence or level of effector molecules from effector immune cells stimulated by an antigen of interest, such as an antigen associated with a disease or condition. The assay involves the use of a basic peptide structure capable of binding to cell lipopolysaccharides or a chemical analog or functional equivalent thereof in combination with the antigen against which the immune response is measured. The assay may also include an immune response stimulant such as a synthetic or double-stranded RNA (e.g. poly(I:C)). Provided herein is a means to determine the enhanced specific responsiveness of cell-mediated immune activity in a subject and, in turn, provides a means for the diagnosis of infectious diseases, pathological conditions, level of immunocompetence and a marker of immune cell responsiveness to endogenous or exogenous antigen as well as assessing exposure to a toxic agent such as beryllium with reduced incidence of non-specific immune reactivity.

Accordingly, an aspect taught herein contemplates a method for measuring cell-mediated immune response activity in a subject, the method comprising contacting a source of immune cells from the subject with an antigen to which the cell-mediated immune response is to be tested in combination with a basic peptide structure capable of binding to cell lipopolysaccharides or a chemical analog or functional equivalent thereof and measuring the presence or elevation in the level of an immune effector molecule from immune cells wherein the presence or level of the immune effector molecule is indicative of the level of cell-mediated responsiveness of the subject.

Another aspect enabled herein provides a method for measuring cell-mediated immune response activity in a subject, the method comprising contacting a source of immune cells from the subject with an antigen to which the cell-mediated immune response is to be tested in combination with a basic peptide structure capable of binding to cell lipopolysaccharides or a chemical analog or functional equivalent thereof and measuring the presence or elevation in the level of an immune effector molecule from immune cells wherein the presence or level of the immune effector molecule is indicative of the level of cell-mediated responsiveness of the subject wherein the level of responsiveness is indicative of the presence or absence or level or stage of a disease or condition selected from the list comprising an infection by a pathogenic agent, an autoimmune disease, a cancer, an inflammatory condition and exposure to a toxic agent.

Still another aspect contemplated herein is an assay to detect the presence, absence, level or stage of a disease or condition in a subject, the method comprising contacting a source of immune cells from the subject with an antigen to which a cell-mediated immune response is to be tested in combination with a basic peptide structure capable of binding to cell lipopolysaccharides or a chemical analog or functional equivalent thereof and measuring the presence or elevation in the level of an immune effector molecule from immune cells wherein the presence or level of the immune effector molecule is indicative of the disease or condition.

Even yet another aspect taught by the present specification is a method for measuring cell-mediated immune response activity in a subject in the presence of potential immune stimulant contaminants such as an endotoxin, the method comprising contacting a source of immune cells from the subject with an antigen to which the cell-mediated immune response is to be tested in the presence of a basic peptide structure capable of binding to cell lipopolysaccharides and measuring the presence or elevation in the level of an immune effector molecule from immune ells wherein the presence or level of the immune effector molecule is indicative of the level of cell-mediated responsiveness of the subject.

Reference to "immune cells" includes lymphocytes of the specific immune system such as T-cells including sub-types of T-cells as well as lymphocytes and other cytotoxic cells of the innate immune system such as NK cells.

Reference to an "immune stimulant contaminant" includes endotoxins which may be portions comprising a cell wall or membrane or may be an antigenic chemical formed within or exported or released from a cell. the contaminants may be part of the collection. In addition to these embodiments, an immune response stimulant may also be added. This is particularly to enhance the response to the antigen. An example includes a synthetic or naturally occurring nucleic acid molecule. An example of a synthetic nucleic acid molecule is a polyinosinic acid-polycytidylic acid (poly(I:C)). The poly(I:C) may be from low to high molecular weight. Reference to "low" molecular weight means less than about 1.5 kilobase (kb) such as from about 0.2 to 1.5 kb. A "high" molecular weight means greater than 1.5 kb such as from about 1.5 to 12 kb including 1.5 to 8 kb. A high molecular weight poly(I:C) is particularly useful in accordance with the present disclosure.

Hence, another aspect described herein is a method for measuring cell-mediated immune response activity in a subject, the method comprising contacting a source of immune cells from the subject with an antigen to which the cell-mediated immune response is to be tested in combination with a basic peptide structure capable of binding to cell lipopolysaccharides or a chemical analog or functional equivalent thereof and an immune response stimulant and measuring the presence or elevation in the level of an immune effector molecule from immune cells wherein the presence or level of the immune effector molecule is indicative of the level of cell-mediated responsiveness of the subject.

Another aspect enabled herein provides a method for measuring cell-mediated immune response activity in a subject, the method comprising contacting a source of immune cells from the subject with an antigen to which the cell-mediated immune response is to be tested in combination with a basic peptide structure capable of binding to cell lipopolysaccharides or a chemical analog or functional equivalent thereof and an immune response stimulant and measuring the presence or elevation in the level of an immune effector molecule from immune cells wherein the presence or level of the immune effector molecule is indicative of the level of cell-mediated responsiveness of the subject wherein the level of responsiveness is indicative of the presence or absence or level or stage of a disease or condition selected from the list comprising an infection by a pathogenic agent, an autoimmune disease, a cancer, an inflammatory condition and exposure to a toxic agent.

Still another aspect described by the present specification contemplates an assay to detect the presence, absence, level or stage of a disease or condition in a subject, the method comprising contacting a source of immune cells from the subject with an antigen to which a cell-mediated immune response is to be tested in combination with a basic peptide structure capable of binding to cell lipopolysaccharides or a chemical analog or functional equivalent thereof and an immune response stimulant and measuring the presence or elevation in the level of an immune effector molecule from T-cells wherein the presence or level of the immune effector molecule is indicative of the disease or condition.

Even yet another aspect enabled by the present specification provides a method for measuring cell-mediated immune response activity in a subject in the presence of potential immune stimulant contaminants such as an endotoxin, the method comprising contacting a source of immune cells from the subject with an antigen to which the cell-mediated immune response is to be tested in the presence of a basic peptide structure capable of binding to cell lipopolysaccharides or a chemical analog or functional equivalent thereof and measuring the presence or elevation in the level of an immune effector molecule from immune cells wherein the presence or level of the immune effector molecule is indicative of the level of cell-mediated responsiveness of the subject.

As indicated above, an example of an immune response stimulant is poly(I:C) or other synthetic or naturally occurring nucleic acid molecule. In a particular embodiment, high molecular weight poly(I:C) is used.

Reference to a basic peptide structure capable of binding to cell lipopolysaccharides includes a cationic detergent-like antibiotic such as a member of the polymyxin B family of antibiotics such as polymyxin B itself or a chemical analog or functional equivalent thereof. A "chemical analog" and a "functional equivalent" means that the molecules behave in a similar manner to polymyxin B by reducing non-specific immune effector molecule production. Functional molecules are those which bind to cell lipopolysaccharides and, in an embodiment, inactivates them. Reference to "polymyxin B" includes N-[4-amino-1-[[1-[[4-amino-1-oxo-1-[[6,9,18-tris(2-aminoethyl)-15-benzyl-3-(1-hydroxyethyl)-12-(2-methylpropyl)-2,5,8,11,14,17,20-heptaoxo-1,4,7,10,13,16,19-heptazacyclotricos-21-yl]amino]butan-2-yl]amino]-3-hydroxy-1-oxobutan-2-yl]amino]-1-oxobutan-2-yl]-6-methyloctanamide. Another example of a basic peptide is a member of the sushi peptide defined by the amino acid sequence set forth in SEQ ID NO:1.

A use is also provided for polymyxin B or a chemical analog or functional equivalent thereof or a sushi peptide or a chemical analog or functional equivalent thereof and optionally an agent which modulates the function or activity of immune cells or a subset of immune cells in the manufacture of a diagnostic assay of cell-mediated immune responsiveness by the method of incubating an antigen or mitogens with a source comprising the immune cells and detecting the presence or elevation in effector molecules.

This use includes the use for detecting or monitoring the presence, absence, level or stage of a disease or condition such as an infection by a pathogenic agent, an autoimmune disease, a cancer, an inflammatory condition and/or exposure to a toxic agent such as a beryllium.

An assay is taught herein to measure the level of an immune response, the immune response including a specific or innate immune response, the method comprising:
(i) collecting a source of immune cells including lymphocytes, the lymphocytes comprising T-cells or NK cells or other cells of the specific or innate immune pathway;
(ii) incubating the cells in the presence of an antigen;
(iii) including a peptide or functional or chemical equivalent which binds to a cell lipopolysaccharide such as polymyxin B or a sushi peptide or a functional or chemical equivalent;
(iv) optionally including an immune stimulant such as a synthetic or double-stranded RNA for example poly(I:C); and
(v) measuring the level or presence of an immune effector molecule indicative of the activity of the immune response.

Hence, the assay may also be conducted in the presence of an agent which modulates the activity or function of a sub-set of immune cells and in particular T-reg cells.

Reference to the modulation of T-cell function or activity includes modulating regulatory T-cell (T-reg cells). It encompasses inhibiting the suppressor function of T-reg cells. Furthermore, measuring "an immune effector molecule" includes measuring one or more different types of molecules.

Another aspect enabled by the present specification is a method for measuring cell-mediated immune response activity in a subject, the method comprising contacting a source of T-cells from the subject with polymyxin B or a sushi peptide or a chemical analog or functional equivalent thereof and optionally an agent which modulates the function or activity of regulatory T-cells or a subset thereof and an antigen to which the cell-mediated response is to be tested and measuring the presence or elevation of the level of an immune effector molecule from T-cell cells wherein the presence or level of the immune effector molecule is indicative of the level of cell-mediated responsiveness of the subject.

Still another aspect taught herein is a method for measuring cell-mediated immune response activity in a subject, the method comprising contacting a source of T-cells from the subject with polymyxin B or a sushi peptide or a chemical analog or functional equivalent thereof and optionally an agent which modulates the function or activity of regulatory T-cells or a subset thereof and an antigen to which the cell-mediated immune response is to be tested and measuring the presence or elevation in the level of an immune effector molecule from T-cells wherein the presence or level of the immune effector molecule is indicative of the level of cell-mediated responsiveness of the subject wherein the level of responsiveness is indicative of the presence or absence or level or stage of a disease or condition selected from the list comprising an infection by a pathogenic agent, an autoimmune disease, a cancer, an inflammatory condition and exposure to atoxic agent.

Even yet another aspect described herein contemplates an assay to detect the presence, absence, level or stage of a disease or condition in a subject, the method comprising contacting a source of T-cells from the subject with polymyxin B or a sushi peptide or a chemical analog or functional equivalent thereof and optionally an agent which modulates the function or activity of regulatory T-cells or a subset thereof and an antigen to which a cell-mediated immune response is, to be tested and measuring the presence or elevation in the level of an immune effector molecule from T-cells wherein the presence or level of the immune effector molecule is indicative of the disease or condition.

Another aspect provides a method for detecting the presence, absence, level or stage of a disease or condition in a human subject in the presence of a potential immune stimulant contaminant such as an endotoxin the method comprising contacting whole blood, which comprises at least 10% of the total volume in a reaction mixture, with polymyxin B or a sushi peptide or a chemical analog or functional equivalent thereof and optionally an agent which inhibits regulatory T-cell function and an antigen to which a cell-mediated immune response is to be tested and measuring the presence or elevation in the level of an immune effector molecule from T-cells wherein the presence or level of the immune effector molecule is indicative of the disease or condition.

In an embodiment, the T-reg cells are immune response suppressor cells the activity of which is inhibited. As indicated above, the assay may be conducted in the presence of an immune response stimulant such as but not limited to a synthetic or naturally occurring nucleic acid molecule. In an embodiment, the stimulant is high poly(I:C). In a particular embodiment, high molecular weight poly(I:C) is used, such as greater than 1.5 kb.

In an embodiment, a method is enabled for measuring cell-mediated immune response activity in a subject, the method comprising contacting a source of T-cells with polymyxin B or a sushi peptide or a chemical analog or functional equivalent thereof and optionally an agent selected from (i) an inhibitor of suppressor regulatory T-cells; and (ii) an activator of immune augmenting cells or a subset thereof; and further contacting T-cells with an antigen to which the cell-mediated response is to be tested and measuring the presence or elevation in the level of an immune effector molecule from T-cells wherein the presence or level of the immune effector molecule is indicative of the level of cell-mediated responsiveness of the subject.

Another embodiment provides a method for measuring cell-mediated immune response activity in a subject, the method comprising contacting a source of T-cells from the subject with polymyxin B or a sushi peptide or a chemical analog or functional equivalent thereof and optionally an agent selected from (i) an inhibitor of suppressor regulatory T-cells; and (ii) an activator of immune augmenting cells or a subset thereof; and further contacting T-cells with an antigen to which the cell-mediated response is to be tested and measuring the presence or elevation in the level of an immune effector molecule from T-cells wherein the presence or level of the immune effector molecule is indicative of the presence, absence, level or stage of a disease or condition.

In a related embodiment, there is provided a use of an agent selected from polymyxin B or a sushi peptide or a chemical analog or functional equivalent thereof and optionally an inhibitor of suppressor regulatory T-cells; and (ii) an activator of cells which augment the immune system or a subset thereof; in the manufacture of a diagnostic assay of cell-mediated immune responsiveness by the method of incubating an antigen or mitogens with a source comprising the T-cells and detecting the presence or elevation in effector molecules.

All such methods are useful to reduce false positive results when the assay is conducted in the presence of an immune stimulant contaminant such as an endotoxin. Furthermore, the antigen-specific response can be enhanced by the addition of an immune response stimulant such as poly(I:C). In an embodiment, the poly(I:C) is a high molecular weight poly(I:C). This includes a poly(I:C) with a molecular weight of greater than about 1.5 kb such as from 1.5-12 kb including 1.5-8 kb.

Reference to a "subject" includes a human or non-human species including primates, livestock animals (e.g. sheep, cows, pigs, horses, donkey, goats), laboratory test animals (e.g. mice, rates, rabbits, guinea pigs, hamsters), companion animals (e.g. dogs, cats), avian species (e.g. poultry birds, aviary birds), reptiles and amphibians. The present disclosure has applicability, therefore, in human medicine as well as having livestock and veterinary and wild-life applications. In an embodiment, the subject is a human and the cell-mediate immune response assay has applications in screening for responsiveness to pathogenic microorganisms, viruses and parasites, toxic agents (e.g. toxicants) potential for development or monitoring autoimmune conditions, Celiac's disease and for monitoring a subject's response to oncological challenge.

The immune effector molecules may be any of a range of molecules which are produced in response to cell activation or stimulation by an antigen. Although an interferon (IFN) such as IFN-γ is a particularly useful immune effector molecule, others include a range of cytokines such as interleukins (IL), e.g. IL-2, IL-4, IL-6, IL-10, IL-12 or IL-13, tumor necrosis factor alpha (TNF-α), transforming growth factor beta (TGF-β), a colony stimulating factor (CSF) such as granulocyte (G)-CSF or granulocyte macrophage (GM)-CSF amongst many others such as complement or components in the complement pathway.

Examples of inhibitors or modulators of T-reg function include CD25 and CTLA4 ligands such as but not limited to a polyclonal or monoclonal antibody to CD25 or CTLA4 or an antigen-binding fragment thereof, humanized or deimmunized polyclonal or monoclonal antibodies to CD25 or CTLA4 or a recombinant or synthetic form of the polyclonal or monoclonal antibodies. Other examples of agents include sense or antisense nucleic and molecules directed to the mRNA or DNA (i.e. genetic material) encoding Janus Tyrosine Kinase 1 (JAK1) or Tyrosine Kinase 2 (TYK2) or small molecule inhibitors of JAK1 or TYK2 proteins. Reference to "small molecules" includes immunoglobulin new antigen receptors (IgNARs) as described in International Patent Publication No. WO 2005/118629. Yet still further examples of suitable agents stimulating agents such as CpG molecules which act via Toll-like receptors (TLRs) and/or other mechanisms.

A single type of agent may be used or two or more types of agents may be employed. For example, the assay may be conducted with a CD25 ligand or CTLA4 ligand and a JAK1/TYK2 sense or antisense oligonucleotide; a CD25 ligand or CTLA4 ligand and a TLR modulating agent; a JAK1/TYK2 sense or antisense oligonucleotide and a TLR modulating agent; or a CD25 ligand or CTLA4 ligand, a JAK1/TYK2 sense or antisense oligonucleotide and a TLR modulating agent. Alternatively, just one type of agent is employed. In another alternative, a CpG comprising oligonucleotide and a TLR modulating agent is used.

The oligonucleotides may be modified such as having a chemically modified backbone such as a phosphorate backbone and/or chemically modified nucleosides or nucleotides.

A "CpG molecule" means an oligonucleotide comprising a CpG sequence or motif. The present disclosure extends to any modulator of Toll-like receptor (TLR) function or other aspect of the immune system.

These aspects include using the above-mentioned particular agents in detecting the presence or absence or level or stage of a disease or condition in a subject such as infection by a pathogenic agent, an autoimmune disease, cancer, an inflammatory agent or exposure to a toxic agent such as beryllium.

The agents such as polymyxin B or a sushi peptide or a chemical analog or functional equivalent thereof or CD25 ligand, antisense molecules and CpG molecules may be free standing in a reactive vessel or may be immobilized to a solid support such as a bead or a side or bottom of a reaction vessel. The agent may also be in dried form which is re-constituted prior to or during use. Similarly, the antigen may be free standing or immobilized in a reactive vessel such as to the vessel itself or a bead or other solid support.

In an embodiment, the sample collected from the subject is generally deposited into a blood collection tube. A blood collection tube includes a blood draw tube or other similar vessel. Conveniently, when the sample is whole blood, the blood collection tube is heparinized. The blood collection tube may also, comprise dried simple sugar such as dextrose. Alternatively, the simple sugar may be added to the tube in a dried form. Alternatively, heparin is added to the tube after the blood is collected. Notwithstanding that whole blood is particularly contemplated and a most convenient sample, the present disclosure extends to other samples containing immune cells such as lymph fluid, cerebral fluid, tissue fluid and respiratory fluid including nasal and pulmonary fluid as well as samples having undergone cell depletion. Reference to "whole blood" includes whole blood which has not been diluted such as with tissue culture, medium, reagents, excipients, etc. In one embodiment, the term "whole blood" includes an assay sample (i.e. reaction mixture) comprising at least 10% by volume whole blood. The term "at least 10% by volume" includes blood volumes of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% by volume of total assay volume of the reaction mixture. Additional agents may be added such as culture media, enzymes, excipients antigen and the like without departing from the sample comprising "whole blood".

An aspect taught herein is the potential for the blood collection tubes or the blood itself to contain immune stimulant contaminants such as endotoxins. The present method mitigates against false positives due to these contaminants. By "mitigates" includes reducing the level or degree of non-specific immune stimulation compared to the level or degree in the absence of polymyxin B or a sushi peptide.

The use of blood collection tubes is compatible with standard automated laboratory systems and these are amenable to analysis in large-scale and random access sampling. Blood collection tubes also minimize handling costs and reduce laboratory exposure to whole blood and plasma and, hence, reduce the risk of laboratory personnel from contracting a pathogenic agent such as HIV or hepatitis B virus (HBV) or hepatitis C virus (HCV).

Combining the incubation step with the collection tube is efficacious and enhances the sensitivity of the assay as does the optional feature of incubating the cells in the presence of a simple sugar such as dextrose or glucose. Generally, the simple sugar is dried into the inside wall of the collection tube. Alternatively, the sugar in dried form is added to the tube or blood sample or reagents.

The cells of the cell-mediated immune system lose the capacity to mount an immune response in whole blood after extended periods following blood draw from the subject, and responses without intervention are often severely reduced or absent 24 hours following blood draw. The reduction of labor and need for specialized plastic ware allows cell-mediated immune stimulation with antigens to be performed at the point of care locations such as physicians' offices, clinics, outpatient facilities and veterinary clinics or on farms. Once antigen stimulation is complete, the requirement for fresh and active cells no longer exists. IFN-γ and other cytokines or immune effector molecules are stable in plasma and, thus, the sample can be stored, or shipped without special conditions or rapid time requirements in a similar fashion to standard serum samples used for other infectious disease or other disease diagnosis. Importantly, the use of polymyxin B or its chemical analogs, or functional equivalents reduces the risk of false positives, such as due to contamination with immune stimulatory agents, including endotoxins.

The incubation step may be from 5 to 50 hours, such as 5 to 40 hours or 8 to 24 hours or a time period in between including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 hours.

The ability to measure specific cell-mediated immunity is important for assessing a subject's ability to respond to an infection by a pathogenic agent such as a microorganism or virus or parasite, to mount an autoimmune response such as in autoimmune diabetes or to protect against cancers or other oncological conditions or to detect an inflammatory condition or to detect exposure or sensitivity of a subject to a toxic agent such as beryllium. It is important in reducing the risk of mis-diagnoses to ensure that the incidence of non-specific effector molecule production is as low as possible. Reference to "measuring a cell-mediated immune response in a subject" includes and encompasses immune diagnosis of infectious and autoimmune diseases, a marker for immunocompetence and the detection of T-cell responses to endogenous and/or exogenous antigens (including a measure of the efficacy of a vaccine) as well as a marker for inflammatory diseases, cancer and toxic agents. Importantly, by inhibiting suppressor T-reg cells or stimulating cells which augment the immune system, the assay's sensitivity is enhanced. Hence, low level infections, for example, can now be detected.

Pathogenic or infectious agents include bacteria, parasites and viruses. Examples of bacteria include Gram positive and Gram negative microorganisms such as *Mycobacterium* species, *Staphylococcus* species, *Streptococcus species*, *Escherichia coli*, *Salmonella* species, *Clostridium* species, *Shigella* species, *Proteus* species, *Bacillus* species, *Hemophilus* species, amongst others. *Mycobacterium tuberculosis* is a particularly useful target as well as conditions arising from infection by *M. tuberculosis* such as tuberculosis (TB). Examples of viruses include Hepatitis virus (Hepatitis B virus and Hepatitis C virus), Herpes virus and Human immune deficiency virus (HIV) as well as diseases resulting therefrom. Parasites include *Plasmodium* species, ringworm, liver parasites and the like. Other pathogenic agents include eukaryotic cells such as yeasts and fungi.

Autoimmune diseases contemplated herein for detection include inter alia alopecia areata, ankylosing spondylitis, antiphospholipid syndrome, autoimmune Addison's disease multiple sclerosis, autoimmune disease of the adrenal gland, autoimmune hemolytic anemia, autoimmune hepatitis, autoimmune oophoritis and orchitis, Behcet's disease, bullous pemphigoid, cardiomyopathy, celiac sprue-dermatitis, chronic fatigue syndrome (CFIDS), chronic inflammatory demyelinating, chronic inflammatory polyneuropathy, Churg-Strauss syndrome, cicatricial pemphigoid, crest syndrome, cold agglutinin disease, Crohn's disease, irritable bowel syndrome, inflammatory bowel disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), lichen planus, lupus, Meniere's disease, mixed connective tissue disease, multiple sclerosis, myasthenia gravis, myocarditis, pemphigus vulgaris, pernicious anemia, polyarteritis nodosa, polychondritis, polyglancular syndromes, polymyalgia rheumatica, polymyositis and dermatomyositis, pochitis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, systemic lupus erythematosus, Takayasu arteritis, temporal arteritis/giant cell arteritis, ulcerative colitis, uveitis, vasculitis and vitiligo.

It is generally important to assess the potential or actual cell-mediated responsiveness in these individuals. The method of the present disclosure can also be used to detect the presence or absence of these conditions as well as the level or stage of disease process. It is important to avoid non-specific effector molecule production. Polymyxin B or its chemical analogs or functional equivalents achieves a reduction in the incidence of non-specific immune response reactivity.

Other disease conditions contemplated include inflammatory disease conditions.

Examples of inflammatory disease conditions contemplated by the present disclosure include but are not limited to those disease and disorders which result in a response of redness, swelling, pain, and a feeling of heat in certain areas that is meant to protect tissues affected by injury or disease. Inflammatory diseases which can be treated using the methods of the present disclosure, include, without being limited to, acne, angina, arthritis, aspiration pneumonia, disease, empyema, gastroenteritis, inflammation, intestinal flu, NEC, necrotizing enterocolitis, pelvic inflammatory disease, pharyngitis, PID, pleurisy, raw throat, redness, rubor, sore throat, stomach flu and urinary tract infections, chronic inflammatory demyelinating polyneuropathy, chronic inflammatory demyelinating polyradiculoneuropathy, chronic inflammatory demyelinating polyneuropathy, chronic inflammatory demyelinating polyradiculoneuropathy.

Cancer therapy also is somewhat dependent on cell-mediated immunity and for which the incidence of false positives needs to be avoided. Cancers contemplated herein include: a group of diseases and disorders that are characterized by uncontrolled cellular growth (e.g. formation of tumor) without any differentiation of those cells into specialized and different cells. Such diseases and disorders include ABL1 protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-Cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extrahepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, hematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer; urethral cancer, urinary system cancer, uroplakins, uterine sarcoma, uterus cancer, vaginal cancer, vulva cancer, Waldenstrom's-macroglobulinemia and Wilms' tumor.

Any of a range of antigens may be employed in the assay such as those specific for a particular organism, virus, autoantigen or cancer cell. Alternatively, more general agents may be used to test generic capacity of a cell-mediated immune response and such agents include mitogens. Examples of the latter include purified protein derivative (PPD) from *Mycobacterium tuberculosis* and tetanus toxoid. In general, however, any peptide, polypeptide or protein, carbohydrate, glycoprotein, phospholipid, phosphoprotein or phospholipoprotein or non-protein chemical agent may be used in the assay system as the antigen or mitogen.

As stated above, detection of the immune effector molecules may be made at the protein or nucleic acid levels. Consequently, reference to "presence or level" of the immune effector molecule includes direct and indirect data. For example, high levels of cytokine mRNA are indirect data showing increased levels of the cytokine.

Ligands to the immune effectors are particularly useful in detecting and/or quantitating these molecules. Antibodies to the immune effectors are particularly useful. Techniques for the assays contemplated herein are known in the art and include, for example, radioimmunoassay, sandwich assays, ELISA and ELISpot. Reference to "antibodies" includes parts of antibodies, mammalianized (e.g. humanized) antibodies, deimmunized antibodies, recombinant or synthetic antibodies and hybrid and single chain antibodies. For skin tests, in humans, humanized or deimmunized antibodies are particularly contemplated herein to detect effector molecules.

Both polyclonal and monoclonal antibodies are obtainable by immunization with the immune effector molecules or antigenic fragments thereof and either type is utilizable for immunoassays. The methods of obtaining both types of sera are well known in the art. Polyclonal sera are less preferred but are relatively easily prepared by injection of a suitable laboratory animal with an effective amount of the immune effector, or antigenic part thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly useful because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

An aspect enabled herein is a method for detecting an immune effector molecule in a sample comprising immune cells from a subject, the method comprising contacting the sample or an aliquot of the sample with an antibody specific for the immune effector molecule or an antigenic fragment thereof for a time and under conditions sufficient for an antibody-effector complex to form, and then detecting the complex wherein the immune effector molecule is generated after incubation of an antigen with immune cells together with a cationic detergent-like antibiotic or a chemical analog or functional equivalent thereof.

A "sample" includes whole blood or a fraction thereof. This method includes, micro-arrays and macro-arrays on planar or spherical solid supports. A micro- or macro-array is useful.

A wide range of immunoassay techniques are available as can be seen by reference to U.S. Pat. Nos. 4,016,043; 4,424,279 and 4,018,653.

The following is a description of one type of assay. An unlabeled antibody is immobilized on a solid substrate and the sample to be tested for the immune effector molecules (e.g. cytokines) brought into contact with the bound molecule. After a suitable period of incubation, for a period of time sufficient to allow formation of an antibody-immune effector molecule complex, a second antibody specific to the effector molecule, labeled with a reporter molecule capable of producing a detectable signal, is then added and incubated, allowing time sufficient for the formation of another complex of antibody-effector-labeled antibody. Any unreacted material is washed away, and the presence of the effector molecule is determined by observation of a signal produced by the reporter molecule. The results may either be qualitative, by simple observation of the visible signal, or may be quantitated by comparing with a control sample containing known amounts of antigen. This generalized technique is well known to those skilled in the art as would be any of a number of variations.

In these assays, a first antibody having specificity for the instant immune effectors is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, spheres, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-120 minutes or where more convenient, overnight) and under suitable conditions (e.g. for about 20° C. to about 40° C.) to allow binding of any subunit present in the antibody. Following the incubation period, the antibody subunit solid phase is washed and dried and incubated with a second antibody specific for a portion of the effector molecule. The second antibody is linked to a reporter molecule which is used to indicate the binding of the second antibody to the effector molecule.

There are many variations to this assay. One particularly useful variation is a simultaneous assay where all or many of the components are admixed substantially simultaneously. Furthermore, binding of an antibody to a cytokine may be determined by binding of a labeled antibody directed to the first mentioned antibody.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. Examples of suitable fluorophores are provided in Table 1. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. Again, the present disclosure extends to a substantially simultaneous assay.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. The fluorescent labeled antibody is allowed to bind to the first antibody-antigen complex. After washing off the unbound reagent, the remaining tertiary complex is then exposed to the light of the appropriate wavelength the fluorescence observed indicates the presence of the antigen of interest. Immunofluorescence and enzyme immunoassay techniques are both very well established in the art and are particularly preferred for the present method. However, other reporter molecules, such as radio-isotope, chemiluminescent or bioluminescent molecules, may also be employed.

There are a range of other detection systems which may be employed including colloidal gold and all such detection systems are encompassed by the present disclosure.

The present method may also use genetic assays such as involving PCR analysis to detect RNA expression products of a genetic sequence encoding an immune effector.

In one embodiment, PCR is conducted using pairs of primers, one or both of which are generally labeled with the same or a different reporter molecule capable of giving a distinguishable signal. The use of fluorophores is particularly useful in the practice of the present disclosure. Examples of suitable fluorophores may be selected from the list given in Table 2. Other labels include luminescence and phosphorescence as well as infrared dyes. These dyes or fluorophores may also be used as reporter molecules for antibodies.

TABLE 2

List of suitable fluorophores

| Probe | $Ex^1$ (nm) | $Em^2$ (nm) |
|---|---|---|
| Reactive and conjugated probes | | |
| Hydroxycoumarin | 325 | 386 |
| Aminocoumarin | 350 | 455 |
| Methoxycoumarin | 360 | 410 |
| Cascade Blue | 375; 400 | 423 |
| Lucifer Yellow | 425 | 528 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| APC-Cy7 conjugates | 650; 755 | 767 |
| Red 613 | 480; 565 | 613 |
| Fluorescein | 495 | 519 |
| FluorX | 494 | 520 |
| BODIPY-FL | 503 | 512 |
| TRITC | 547 | 574 |
| X-Rhodamine | 570 | 576 |
| Lissamine Rhodamine B | 570 | 590 |
| PerCP | 490 | 675 |
| Texas Red | 589 | 615 |
| Allophycocyanin (APC) | 650 | 660 |
| TruRed | 490, 675 | 695 |
| Alexa Fluor 350 | 346 | 445 |
| Alexa Fluor 430 | 430 | 545 |
| Alexa Fluor 488 | 494 | 517 |
| Alexa Fluor 532 | 530 | 555 |
| Alexa Fluor 546 | 556 | 573 |
| Alexa Fluor 555 | 556 | 573 |
| Alexa Fluor 568 | 578 | 603 |
| Alexa Fluor 594 | 590 | 617 |
| Alexa Fluor 633 | 621 | 639 |
| Alexa Fluor 647 | 650 | 688 |
| Alexa Fluor 660 | 663 | 690 |
| Alexa Fluor 680 | 679 | 702 |
| Alexa Fluor 700 | 696 | 719 |
| Alexa Fluor 750 | 752 | 779 |
| Cy2 | 489 | 506 |
| Cy3 | (512); 550 | 570; (615) |
| Cy3,5 | 581 | 596; (640) |
| Cy5 | (625); 650 | 670 |
| Cy5,5 | 675 | 694 |
| Cy7 | 743 | 767 |
| Nucleic acid probes | | |
| Hoeschst 33342 | 343 | 483 |
| DAPI | 345 | 455 |
| Hoechst 33258 | 345 | 478 |
| SYTOX Blue | 431 | 480 |
| Chromomycin A3 | 445 | 575 |
| Mithramycin | 445 | 575 |
| YOYO-1 | 491 | 509 |
| SYTOX Green | 504 | 523 |
| SYTOX Orange | 547 | 570 |
| Ethidium Bormide | 493 | 620 |
| 7-AAD | 546 | 647 |
| Acridine Orange | 503 | 530/640 |
| TOTO-1, TO-PRO-1 | 509 | 533 |
| Thiazole Orange | 510 | 530 |
| Propidium Iodide (PI) | 536 | 617 |
| TOTO-3, TO-PRO-3 | 642 | 661 |
| LDS 751 | 543; 590 | 712; 607 |
| Fluorescent Proteins | | |
| Y66F | 360 | 508 |
| Y66H | 360 | 442 |
| EBFP | 380 | 440 |
| Wild-type | 396, 475 | 50, 503 |
| GFPuv | 385 | 508 |
| ECFP | 434 | 477 |
| Y66W | 436 | 485 |
| S65A | 471 | 504 |
| S65C | 479 | 507 |
| S65L | 484 | 510 |
| S65T | 488 | 511 |
| EGFP | 489 | 508 |
| EYFP | 514 | 527 |
| DsRed | 558 | 583 |
| Other probes | | |
| Monochlorobimane | 380 | 461 |
| Calcein | 496 | 517 |

[1]Ex: Peak excitation wavelength (nm)
[2]Em: Peak emission wavelength (nm)

Any suitable method of analyzing fluorescence emission is encompassed by the present disclosure. In this regard, the disclosure contemplates techniques including but not restricted to 2-photon and 3-photon time resolved fluorescence spectroscopy as, for example, disclosed by Lakowicz et al, *Biophys. J.* 72:567, 1997, fluorescence lifetime imaging as, for example, disclosed by Eriksson et al, *Biophys. J.* 2:64, 1993 and fluorescence resonance energy transfer as, for example, disclosed by Youvan et al, *Biotechnology et elia* 3:1-18, 1997.

Luminescence and phosphorescence may result respectively from a suitable luminescent or phosphorescent label as is known in the art. Any optical means of identifying such label may be used in this regard.

Infrared radiation may result from a suitable infrared dye. Exemplary infrared dyes that may be employed in the disclosure include but are not limited to those disclosed in Lewis et al, *Dyes Pigm.* 42(2):197, 1999, Tawa et al, *Mater. Res. Soc. Symp. Proc.* 488 [Electrical, Optical and Magnetic Properties of Organic Solid-State Materials IV], 885-890, Daneshvar et al, *J. Immunol. Methods* 226(1-2):119-128, 1999, Rapaport et al, *Appl. Phys. Lett.* 74(3):329-331, 1999 and Durig et al, *J. Raman Spectrosc.* 24(5):281-285, 1993. Any suitable infrared spectroscopic method may be employed to interrogate the infrared dye. For instance, fourier transform infrared spectroscopy as, for example, described by Rahman et al, *J. Org. Chem.* 63:6196, 1998 may be used in this regard.

Suitably, electromagnetic scattering may result from diffraction, reflection, polarization or refraction of the incident electromagnetic radiation including light and X-rays. Such scattering can be used to quantitate the level of mRNA or level of protein.

Flow cytometry is particularly useful in analyzing fluorophore emission.

As is known in the art, flow cytometry is a high throughput technique which involves rapidly analyzing the physical and chemical characteristics of particles (e.g. labeled mRNA, DNA or proteins) as they pass through the path of one or more laser beams while suspended in a fluid stream. As each particle intercepts the laser beam, the scattered light and fluorescent light emitted by each cell or particle is detected and recorded using any suitable tracking algorithm as, for example, described hereunder.

A modern flow cytometer is able to perform these tasks up to 100,000 cells/particles s$^{-1}$. Through the use of an optical array of filters and dichroic mirrors, different wavelengths of fluorescent light can be separated and simultaneously detected. In addition, a number of lasers with different excitation wavelengths may be used. Hence, a variety of fluorophores can be used to target and examine, for example, different immune effectors within a sample or immune effectors from multiple subjects.

Suitable flow cytometers which may be used in the methods of the present disclosure include those which measure five to nine optical parameters (see Table 3) using a single excitation laser, commonly an argon ion air-cooled laser operating at 15 mW on its 488 nm spectral line. More advanced, flow cytometers are capable of using multiple excitation lasers such as a HeNe laser (633 nm) or a HeCd laser (325 nm) in addition to the argon ion laser (488 or 514 nm).

TABLE 3

Exemplary optical parameters which may be measured by a flow cytometer.

| Parameter | Acronym | Detection angle form incident laser beam | Wavelength (nm) |
| --- | --- | --- | --- |
| Forward scattered light | FS | 2-5° | 488* |
| Side scattered light | SS | 90° | 488* |
| "Green" fluorescence | FL1 | 90° | 510-540† |
| "Yellow" fluorescence | FL2 | 90° | 560-580† |
| "Red" fluorescence | FL3 | 90° | >650# |

*using a 488 nm excitation laser
†width of bandpass filter
longpass filter

For example, Biggs et al, *Cytometry* 36:36-45, 1999 have constructed an 11-parameter flow cytometer using three excitation lasers and have demonstrated the use of nine distinguishable fluorophores in addition to forward and side scatter measurements for purposes of immunophenotyping (i.e. classifying) particles. Parameters commercially available include: forward scatter, side scatter and three excitation lasers each with five fluorescence detectors. Whether all of the parameters can be adequately used depends heavily on the extinction coefficients, quantum yields and amount of spectral overlap between all fluorophores (Malemed et al, "*Flow cytometry and sorting*", 2$^{nd}$ Ed., New York, Wiley-Liss, 1990). However, it will be understood that the method enabled herein is not restricted to any particular flow cytometer or any particular set of parameters. In this regard, the disclosure also contemplates use in place of a conventional flow cytometer, a microfabricated flow cytometer as, for example, disclosed by Fu et al, *Nature Biotechnology* 17:1109-1111, 1999.

The assay taught herein may be automated or semi-automated for high throughput screening or for screening for a number of immune effectors from the one subject. The automation is conveniently controlled by computer software.

Such an algorithm uses relationships between presence or levels of immune effector molecules and immune responsiveness observed in training data (with known immune responsiveness) to infer relationships which are then used to predict the status of subjects with unknown immune responsiveness status. An algorithm is employed which provides an index of probability that a subject has a particular immune response capability. The algorithm performs a multivariate or univariate analysis function.

Hence, in one embodiment, a diagnostic rule is provided based on the application of statistical and machine learning algorithms. Such an algorithm uses the relationships between immune effector molecules and immune response status observed in training data (with known immune responsiveness status) to infer relationships which are then used to predict the status of subjects with unknown status. Practitioners skilled in the art of data analysis recognize that many different forms of inferring relationships in the training data may be used without materially changing the present disclosure.

Contemplated herein is the use of a knowledge base of training data comprising levels of immune effector molecules from a subject with a known level of immune responsiveness or state to generate an algorithm which, upon input of a second knowledge base of data comprising levels of the same immune effector molecules from a subject with an unknown state of immune responsiveness, provides an index of probability that predicts the nature of the immune responsiveness.

The term "training data" includes knowledge of levels of immune effector molecule relative to a control. A "control" includes a comparison to levels of effector molecules in a subject devoid of immune response stimulation or may be a statistically determined level based on trials. The term "levels" also encompasses ratios of levels of immune effector molecules.

Further provided herein is an algorithm-based screening assay to screen samples from patients. Generally, input data are collected based on the presence or levels of an immune effector molecule and subjected to an algorithm to assess the statistical significance of any elevation in levels which information is then output data. Computer software and hardware for assessing input data are encompassed by the present disclosure.

The assay taught herein permits integration into existing or newly developed pathology architecture or platform systems. For example, the subject method allows a user to determine the status of a subject with respect to a immune responsiveness, the method including:

(a) receiving data in the form of levels or concentrations of an immune effector molecule following incubation of immune cells from the subject with an antigen to be tested, an agent which binds to cell polysaccharide and optionally an immune stimulant; from the user via a communications network;

(b) processing the subject data via an algorithm which provides an immune response index value;

(c) determining the status of the subject in accordance with the results of the immune response index value in comparison with predetermined values; and (d) transferring an indication of the status of the subject to the user via the communications network.

Conveniently, the method generally further includes:

(a) having the user determine the data using a remote end station; and (b) transferring the data from the end station to the base station via the communications network.

The base station can include first and second processing systems, in which case the method can include:

(a) transferring the data to the first processing system;
(b) transferring the data to the second processing system; and
(c) causing the first processing system to perform the algorithmic function to generate the immune response index value.

The method may also include:
(a) transferring the results of the algorithmic function to the first processing system; and
(b) causing the first processing system to determine the immune status of the subject.

In this case, the method also includes at lest one of:
(a) transferring the data between the communications network and the first processing system through a first firewall; and
(b) transferring the data between the first and the second processing systems through a second firewall.

The second processing system may be coupled to a database adapted to store predetermined data and/or the algorithm, the method include:
(a) querying the database to obtain at least selected predetermined data or access to the algorithm from the database; and
(b) comparing the selected predetermined data to the subject data or generating a predicted probability index.

The second processing system can be coupled to a database, the method including storing the data in the database.

The method can also include causing the base station to:
(a) determine payment information, the payment information representing the provision of payment by the user; and
(b) perform the comparison in response to the determination of the payment information.

The present method also enables a base station to determine the status of a subject with respect to cell-mediated immune responsiveness, the base station including:
(a) a store method;
(b) a processing system, the processing system being adapted to:
  (i) receive subject data from the user via a communications network, the data including levels or concentrations of an immune effector molecule generated following incubation of immune cells with an antigen to be tested, an agent which binds to a cell lipopolysaccharide and optionally an immune stimulant from a subject;
  (ii) performing an algorithmic function including comparing the data to predetermined data;
  (iii) determining the status of the subject in accordance with the results of the algorithmic function including the comparison; and
(c) output an indication of the status of the subject to the user via the communications network.

The processing system can be adapted to receive data from a remote end station adapted to determine the data.

The processing system may include:
(a) a first processing system adapted to:
  (i) receive the data; and
  (ii) determine the status of the subject in accordance with the results of the algorithmic function including comparing the data; and
(b) a second processing system adapted to:
  (i) receive the data from the processing system;
  (ii) perform the algorithmic function including the comparison; and
  (iii) transfer the results to the first processing system.

The base station typically includes:
(a) a first firewall for coupling the first processing system to the communications network; and
(b) a second firewall for coupling the first and the second processing systems.

The processing system can be coupled to a database, the processing system being adapted to store the data in the database.

Reference to an "algorithm" or "algorithmic functions" as outlined above includes the performance of a single or multivariate analysis function. A range of different architectures and platforms may be implemented in addition to those described above. It will be appreciated that any form of architecture suitable for implementing the present disclosure may be used. However, one beneficial technique is the use of distributed architectures.

It will also be appreciated that in one example, the end stations can be hand-held devices, such as PDAs, mobile phones, or, the like, which are capable of transferring the subject data to the base station via a communications network such as the Internet, and receiving the reports.

In the above aspects, "data" mean the levels or concentrations of the immune effector molecules. The "communications network" includes the interne. When a server is used, it is generally a client server or more particularly a simple object application protocol (SOAP).

An aspect taught herein includes experiments that demonstrate the cell-mediated immune responsiveness of a subject by measuring responsiveness to particular antigens or mitogens in the presence of a basic peptide structure capable of binding to cell lipopolysaccharides such as a polymyxin B or a sushi peptide or chemical analog or functional equivalent thereof. In an embodiment, one or more samples such as a sample of peripheral blood, of enriched white cell fraction of blood or bronchoalveolar lavage may be obtained from a subject having or suspected of development a particular disease (e.g. autoimmune disease, infection to a pathogenic agent or exposure to beryllium) and the immune responsiveness measured by determination of effector molecules from effector immune cells (e.g. $CD4^+$ T-cells, NK cells, cytotoxic lymphocytes). The assay may also be conducted, in an optional embodiment, in the presence of an agent which modulates T-cell function such as regulatory T-cell function.

The immunobinding methods include methods for detecting or quantifying the amount of a reactive component in a sample, which methods require the detection or quantitation of any immunecomplexes formed during the binding process. Here, one would obtain a sample suspected of containing a cytokine and contact the sample with an antibody and then detect or quantify the amount of immunecomplexes formed under the specific conditions.

Contacting the chosen biological sample with the antibody under conditions effective and for a period of time sufficient to allow the formation of immunecomplexes (primary immunecomplexes) is generally a matter of adding the composition to the sample and incubating the mixture for a period of time long enough for the antibodies to form immunecomplexes with, i.e. to bind to, any antigens present. After this time, the sample-antibody composition, such as a tissue section, ELISA plate, ELISpot, dot blot or Western blot, will generally be washed to remove any non-specifically bound antibody species, allowing only those antibodies specifically bound within the primary immunecomplexes to be detected.

In an embodiment, a method is enabled herein for detecting the presence, absence, level or stage of a disease or condition in a human subject, the method comprising contacting whole blood, which comprises at least 10% of the total volume in a reaction mixture, with polymyxin B or a sushi peptide or a chemical analog or functional equivalent thereof and optionally an agent which inhibits regulatory T-cell function and an antigen to which a cell-mediated immune response is to be tested and measuring the presence or elevation in the level of an immune effector molecule from T-cells wherein the presence or level of the immune effector molecule is indicative of the disease or condition.

In a further embodiment, kits are provided for use and, in particular when used with the methods described above. In an embodiment, an immunodetection kit is contemplated. In another embodiment, a kit for analysis of a sample from a subject having or suspected of developing a metal or chemically-induced disease is contemplated. In a more particular embodiment, a kit for analysis of a sample from a subject having or suspected of developing a disease is contemplated. In another embodiment, a kit is for assessing the cell-mediated immune responsiveness of a subject before or after a disease state has developed.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of antigen or effector molecule, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The kit further comprises a basic peptide structure capable of binding to cell lipopolysaccharides such as polymyxin B or a sushi peptide or a chemical analog or functional equivalent thereof.

Accordingly, enabled herein is a kit for measuring a cell-mediate immune response in a subject a kit being in multicomponent form wherein a first component comprises a multiplicity of blood collection tubes, a second component comprises an antibody-based detection means for an immune effector molecule, a third component comprises a polymyxin B or a sushi peptide or a chemical analog or functional equivalent thereof and a fourth component comprises a set of instructions which instructions comprise the steps of according to the present disclosure.

The container means of any of the kits will generally include at least one vial, test tube, flask, bottle, syringe or other container means, into which the testing agent, the antibody or antigen may be placed, and particularly, suitably aliquoted. Where a second or third binding ligand or additional component is provided, the kit also generally contains a second, third or other additional container into which this ligand or component may be placed. The kits of the present disclosure will also typically include a means for containing the antibody, antigen, and any other reagent containers in close confinement for commercial sale. Such containers may include injection or blow-molded plastic containers into which the desired vials are retained. The kits further contain a compartment adapted to contain a polymyxin B or a chemical analog or functional equivalent thereof.

Contemplated herein is an improved assay to detect a cell-mediated immune response or the level thereof in a subject, the assay comprising incubating an antigen with a source of immune cells from the subject and detecting for the presence or elevation in effector molecules, the improvement comprising further incubating the immune cells with a basic peptide structure capable of binding to cell lipopolysaccharides such as polymyxin B or a sushi peptide or a chemical analog or functional equivalent thereof. This improvement reduces the incidence of non-specific effector molecule production. A further improvement optionally comprises incubating the T-cells with an agent which inhibits suppressor T-reg cells or which stimulates cells which augment the immune system.

Enabled herein is a method of treating of a subject having a pathogenic infection, an autoimmune disorder or cancer or a propensity for developing such a condition or disorder, the method comprising contacting a source of immune cells from the subject with a basic peptide structure capable of binding to cell lipopolysaccharides such as polymyxin B or a sushi peptide or a chemical analog or functional equivalent thereof and an antigen to which the cell-mediated immune, response is to be tested and measuring the presence or elevation in the level of an immune effector molecule from the immune cells wherein the presence or level of the immune effector molecule is indicative of the level of cell-mediated responsiveness of the subject which is indicative of the presence, absence, level or state of the condition or disorder and then treating the condition or disorder. The method may further comprise contacting the cells with an agent which modulates the function or activity of T-cells or a subset thereof such as T-reg cells.

Further provided herein is the use of a basic peptide structure capable of binding to cell lipopolysaccharides such as polymyxin B or a sushi peptide or a chemical analog or functional equivalent thereof in the manufacture of a diagnostic assay of cell-mediated immune responsiveness by the method of incubating an antigen or mitogens with a source comprising the immune cells and detecting the presence or elevation in effector molecules.

Described herein is the use of a basic peptide structure capable of binding to cell lipopolysaccharides such as polymyxin B or a sushi peptide or a chemical analog or functional equivalent thereof and an agent selected from (i) an inhibitor of suppressor regulatory T-cells; and (ii) an activator of which augment the immune system or a subset thereof; in the manufacture of a diagnostic assay of cell-mediated immune responsiveness by the method of incubating an antigen or mitogens with a source comprising the T-cells and, detecting the presence or elevation in effector molecules.

Contemplated herein is the use of a blood collection tube comprising exogenously added dried simple sugar such as dextrose or glucose in the performance of an assay to detect immune responsiveness in a subject by the method of contacting a source of immune cells from the subject with a basic peptide structure capable of binding to cell lipopolysaccharides such as polymyxin B or a sushi peptide or a chemical analog or functional equivalent thereof and an antigen to which the cell-mediated immune response is to be tested and measuring the presence or elevation in the level of an immune effector molecule from T-cells wherein the presence or level of the immune effector molecule is indicative of the level of cell-mediated responsiveness of the subject.

The blood collection tube or blood itself may contain immune stimulant contaminants such as endotoxins. This assay reduces the false positives this may cause.

Aspects enabled herein are further described by the following non-limiting Examples.

EXAMPLE 1

Development of Assay

Heparinized blood samples were collected from consenting volunteers or donors. Blood samples were collected into Vacuette [registered trade mark] tubes (Greiner Bio-one, Germany).

Aliquots of the blood samples were incubated with either *Mycobacterium tuberculosis* purified protein derivative (PPD, Cellestis Limited, Australia), Tetanus toxoid (CSL Limited, Australia), phytohemagglutinin (Cellestis Limited, Australia) or saline control in a number of different sized blood collection tubes as well as the standard 24-well tissue culture plates recommended by the manufacturers of the bovine whole blood IFN-γ test (Bovigam [registered trade mark], CSL Ltd.) or the human Quantiferon [registered trade mark] test (Cellestis Limited, Australia).

In some experiments, dextrose was added at various concentrations to the blood before initiation of incubation. Alternatively, the simple sugar is dried in the blood collection tube before blood is added or the sugar is added in dried form to the blood.

Antigen stimulated blood samples were incubated for 16 to 24 hours at 37° C., after which plasma was harvested from above the settled blood cells. The amount of IFN-γ present in each plasma sample was then quantified using the Quantiferon-TB [registered trade mark] ELISA (Cellestis Limited, Australia) as per the manufacturer's instructions. Samples stimulated with the tetanus toxoid antigen and the saline control were also tested using a more sensitive ELISA for IFN-γ (Quantiferon-CMI; Cellestis Limited, Australia) as per the manufacturer's instructions.

ELISA optical density values for IFN-γ standards run on each ELISA plate were used to construct a standard curve from which the amount of IFN-γ present in each of the test plasma samples was converted to IU/mL values.

The samples were also incubated with polymyxin B. In an alternative method, the samples were incubated with the polymyxin B and a CD25 ligand, oligonucleotide directed to genetic material encoding JAK1 or TYK2 or a CpG oligonucleotide. The oligonucleotide may be phosphorothioated.

EXAMPLE 2

Inhibition of IFN-γ Production by Polymyxin B

The effect of polymyxin B on IFN-γ production was assessed. Blood from 8 healthy donors was added to QuantiFERON-CMV blood collection tubes (1.0 mL per tube). One tube for each donor had 1.0 μg/mL of polymyxin B added, whilst the second tube served as a control. Blood was incubated at 37° C. for 20 hours before the tubes were centrifuged and the resultant concentration of IFN-γ determined by ELISA. The results are shown in Table 4.

TABLE 4

IFN-γ concentration (IU/mL) in blood samples containing 1 μg/mL polymyxin B versus control.

| Subject | CMV | CMV + PMB 1.0 μg/mL |
|---------|-------|---------------------|
| 1 | 0.05 | 0.05 |
| 2 | 2.17 | 2.3 |
| 3 | 0.55 | 0.55 |
| 4 | 12.97 | 8.35 |
| 5 | 0.04 | 0.04 |
| 6 | 0.08 | 0.08 |
| 7 | 0.43 | 0.51 |
| 8 | 0.76 | 1.53 |
| 9 | 0.04 | 0.04 |
| 10 | 24.28 | 24.28 |

This Example demonstrated that the addition of 1 μg/mL of polymyxin B does not adversely affect the production of IFN-γ.

EXAMPLE 3

Effects of Polymyxin B on Non-Specific IFN-γ Production

In this Example, blood from 8 healthy donors was collected in Li-Heparin tubes. Aliquots of 1.0 mL were prepared in 13/75 mm plain gel tubes. An endotoxin, lipopolysaccharides (LPS), was added to each tube of blood at a concentration of 1 μg/mL. Various concentrations of polymyxin B were added to each of the tubes. The blood was then incubated at 37° C. for 20 hours before the tubes were centrifuged and the IFN-γ concentration of the plasma determined by ELISA. The results are shown in Table 5.

TABLE 5

IFN-γ concentration (IU/mL) in blood samples containing 1 μg/mL LPS with various concentrations of polymyxin B added.

| | Polymyxin (ug/mL) | | | | |
|---|---|---|---|---|---|
| Subject | 0 | 0.1 | 1 | 10 | 100 |
| 1 | — | 2.00 | 1.17 | 0.36 | 0.05 |
| 2 | — | 0.79 | 0.50 | 0.32 | 0.06 |
| 3 | — | 0.41 | 0.14 | 0.12 | 0.02 |
| 4 | 1.26 | 0.67 | 0.41 | 0.25 | 0.02 |
| 5 | 0.91 | 0.44 | 0.22 | 0.11 | 0.05 |
| 6 | 25.81 | 9.28 | 3.31 | 1.96 | 0.04 |
| 7 | 3.36 | 2.87 | 2.57 | 1.41 | 0.02 |
| 8 | 2.15 | 0.32 | 0.21 | 0.11 | 0.18 |

This Example demonstrated that the addition of polymyxin B to samples containing endotoxin caused a reduction in non-specific IFN-γ production.

EXAMPLE 4

Use of Polymyxin B in IFN-γ Assay

Blood was taken from four healthy donors collected in Li-Heparin tubes. Aliquots of 1.2 mL from each donor was added to a BD heparin tube known to generate non-specific IFN-γ responses due to endotoxin contamination, the same BD tube but with 100 μg/mL polymyxin B added and a Greiner heparin tube as a negative control (which has not been shown to result in non-specific IFN-γ production). Tubes were mixed to resolublize the heparin and to ensure blood contact with tube plastic.

Aliquots of 1.0 mL from each heparin tube type were then transferred to 13/75 mm plain gel tubes. The blood was then incubated at 37° C. for 20 hours before the tubes were centrifuged and the IFN-γ concentration of the plasma determined by ELISA.

TABLE 6

IFN-γ concentration (IU/mL) in blood samples transferred from various heparin tubes.

IFN-gamma (IU/mL)

| Subject | BD Heparin Tube | BD Heparin Tube + 100 μg/mL Polymyxin B | Greiner Heparin Tube |
|---|---|---|---|
| 1 | 2.36 | 0.24 | 0.05 |
| 2 | 6.19 | 0.51 | 0.06 |
| 3 | 0.39 | 0.11 | 0.06 |
| 4 | 0.93 | 0.11 | 0.07 |

This Example demonstrates that the non-specific IFN-γ production observed in BD heparin tubes (known to contain endotoxin), is significantly reduced by the addition of 100 ug/mL polymyxin B.

EXAMPLE 5

Use of Immune Response Stimulant

Heparinized blood samples were collected into Li-Hep Vacuette [registered trade mark] tubes (Greinder Bio-one, Germany).

Aliquots of the blood samples were incubated with 10 μg/ml of high molecular weight poly(I:C) (InvivoGen; dissolved in PBS) in nil blood collection tubes (QuntiFERON [registered trade mark]-TB Gold In-Tube, Cellestis Ltd, Australia), as supplied or spiked with tetanus toxoid (1001 fu/ml), or in CMV tubes (QantiFERON-CMV, Cellestis Ltd, Australia).

Stimulated blood samples were incubated for 16-24 hours at 37° C., after which the tubes were centrifuged and the plasma harvested. The amount of IFN-γ present in each plasma sample was then quantified using either the QuantiFERON [registered trade mark]-TB analysis software (1G) or the QuantiFERON [registered trade mark]-TB Gold analysis software (2G) [Cellestis Ltd, Australia] as per the manufacture's instructions.

ELISA optical density values for IFN-γ standards run on each ELISA plate were used to construct a standard curve from which the amount of IFN-γ present in each of the test plasma samples was converted to IU/mL values.

Tables 7 through 9 present the results from independent experiments assessing the effects of high molecular weight poly(I:C) on the response of whole blood to different antigens (CMV and tetanus toxoid(TT)).

TABLE 7

Experiment 1

(A) PolyI:C at 10 ug/mL

| Donor | TT | PolyIC + TT | ΔTT |
|---|---|---|---|
| 1 | 6.27 | 12.17 | 5.9 |
| 2 | 0.69 | 0.96 | 0.27 |

TABLE 7-continued

Experiment 1

| | | | |
|---|---|---|---|
| 3 | 3.4 | 10.0 | 6.6 |
| 4 | 27.7 | 36.64 | 8.94 |
| 5 | 13.3 | 27.61 | 14.31 |
| 6 | 1.74 | 3.23 | 1.49 |
| 7 | 8.35 | 16.77 | 8.42 |
| 8 | 10.78 | 15.99 | 5.21 |
| 9 | 8.56 | 11.37 | 2.81 |
| 10 | 25.82 | 33.53 | 7.71 |

(B) PolyI:C at 10 ug/mL

| Donor | CMV | PolyIC + CMV | ΔCMV |
|---|---|---|---|
| 1 | 1.39 | 3.02 | 1.63 |
| 2 | 2.59 | 6.54 | 3.95 |
| 3 | 2.88 | 7.48 | 4.6 |
| 4 | 0.25 | 0.29 | 0.04 |
| 5 | 207.3 | 227.2 | 19.9 |
| 6 | 4.76 | 5.02 | 0.26 |

TABLE 8

Experiment 2

(A) PolyI:C at 10 μg/ml

| Donor | TT | TT + poly IC | ΔTT |
|---|---|---|---|
| 1 | 7.59 | 22.79 | 15.2 |
| 2 | 30.49 | 55.26 | 24.77 |
| 3 | 12.33 | 28.73 | 16.4 |
| 4 | 4.74 | 36.99 | 32.25 |
| 5 | 43.37 | 80.03 | 36.66 |
| 6 | 15.96 | 26.31 | 10.35 |
| 7 | 40.51 | 95.12 | 54.61 |

(B) PolyI:C at 10 μg/ml

| Donor | CMV | CMV Poly IC | ΔCMV |
|---|---|---|---|
| 1 | 5.08 | 7.49 | 2.41 |
| 2 | 25.21 | 29.28 | 4.07 |
| 3 | 0.06 | 2.32 | 2.26 |
| 4 | 0.04 | 0.35 | 0.31 |
| 5 | 1.77 | 3.22 | 1.45 |
| 6 | 0.97 | 1.83 | 0.86 |

TABLE 9

Experiment 3

| Donor | Antigen | polyI:C (μg/ml) | IU/mL | Δ |
|---|---|---|---|---|
| 1 | TT | 0 | 10.85 | |
| | | 10 | 45.40 | 34.55 |
| 2 | TT | 0 | 44.67 | |
| | | 10 | 156.92 | 112.25 |
| | CMV | 0 | 14.64 | |
| | | 10 | 42.46 | 27.82 |
| 3 | TT | 0 | 14.85 | |
| | | 10 | 17.65 | 2.8 |
| 4 | CMV | 0 | 0.81 | |
| | | 10 | 8.08 | 7.27 |
| 5 | CMV | 0 | 3.00 | |
| | | 10 | 6.70 | 3.7 |

These examples demonstrate that the addition of poly(I:C) at 10 µg/ml to QuantiFERON [registered trade mark] tubes containing different antigens increases the IFN-γ production. The response to poly(I:C) alone varies between donors but the response in most cases is relatively small. The response to poly(I:C) in conjunction with either cytomegalovirus (CMV) or tetanus toxoid (TT) antigen is greater in most cases than nil controls, poly(I:C) or antigen alone. This supports the combination of high molecular weight poly(I:C) with antigen can boost the IFN-γ production in stimulated whole blood.

EXAMPLE 6

Effects of Sushi Peptide

Heparinized blood samples were collected into Li-Hep Vacuette (registered trade mark) tubes (Greiner Bio-one, Germany).

Aliquots of 1 ml of the blood samples were incubated with various concentrations of Lipopolysaccharide (Sigma, Australia) and a sushi peptide (HAEHKVKIGVEQKYGQFPQGTEVTYTCSGNYFLM) [SEQ ID NO:1] (American Peptide Company, California) in nil blood collection tubes (QuantiFERON [registered trade mark]-TB Gold In-Tube, Cellestis Ltd, Australia) either as supplied or spiked with tetanus toxoid (1001 fu/ml), or in CMV tubes (QuantiFERON-CMV, Cellestis Ltd, Australia).

Stimulated blood samples were incubated for 16-24 hr at 37° C., after which the tubes were centrifuged and the plasma harvested. The amount of IFN-γ present in each plasma sample was then quantified using the QuantiFERON (registered trade mark)-TB Gold ELISA (Cellestis Limited, Australia) as per the manufacturer's instructions.

ELISA optical density values for IFN-γ standards run on each ELISA plate were used to construct a standard curve from which the amount of IFN-γ present in each of the test plasma samples was converted to IU/mL values.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations of any two or more of said steps or features.

BIBLIOGRAPHY

Biggs et al, *Cytometry* 36:36-45, 1999
Daneshvar et al, *J. Immunol. Methods* 226(1-2):119-128, 1999
Durig et al, *J. Raman Spectrosc.* 24(5):281-285, 1993
Eriksson et al, *Biophys. J.* 2: 64, 1993
Fu et al, *Nature Biotechnology* 17:1109-1111, 1999
Lakowicz et al, *Biophys. J.* 72:567, 1997
Lewis et al, *Dyes Pigm.* 42(2):197, 1999
Malemed et al, "*Flow cytometry and sorting*", $2^{nd}$ Ed., New York, Wiley-Liss, 1990
Rahman et al, *J. Org. Chem.* 63:6196, 1998
Rapaport et al, *Appl. Phys. Lett.* 74(3):329-331, 1999
Tawa et al, *Mater. Res. Soc. Symp. Proc.* 488 [Electrical, Optical and Magnetic Properties of Organic Solid-State Materials IV], 885-890
Youvan et al, *Biotechnology et elia* 3:1-18, 1997

The invention claimed is:

1. A method for measuring cell-mediated immune response activity in a subject, said method comprising:
   (a) contacting a sample to be assayed which comprises a source of immune cells that comprise lymphocytes from the subject, with (i) a basic peptide structure capable of binding to cell lipopolysaccharides, wherein the basic peptide is polymyxin B or a polymyxin B antibiotic family member that is a chemical analog of polymyxin B, or a sushi peptide, and (ii) an antigen to which a cell-mediated immune response by said immune cells is to be tested, wherein the source of immune cells is undiluted whole blood collected from the subject, wherein the whole blood comprises from about 50% to 100% by volume of the sample to be assayed, and wherein said step of contacting takes place within 24 hours of collecting the whole blood from the subject, thereby to obtain contacted immune cells;
   (b) adding to said contacted immune cells (iii) an immune response stimulant which comprises a nucleic acid molecule that is polyinosinic acid-polycytidylic acid (polv(I:C)), to enhance the cell-mediated response to the antigen; and
   (c) measuring, in plasma obtained from the whole blood subsequent to step (b), presence or elevation in a level of at least one immune effector molecule from the immune cells, wherein the presence or elevation in the level of the immune effector molecule is indicative of a level of cell-mediated immune responsiveness of the subject, said at least one immune effector molecule being selected from interferon-γ (IFN-γ), IL-2, IL-4, IL-6, IL-10, IL-12, IL-13, TNF-α, TGF-β, (G)-CSF, and (GM)-CSF.

2. The method of claim 1 wherein the polymyxin B comprises N-[4-amino-1-[[1-[[4-amino-1-oxo-1-[[6,9,18-tris(2-aminoethyl)-15-benzyl-- 3-(1-hydroxyethyl)-12-(2-methylpropyl)-2,5,8,11,14,17,20-heptaoxo-1,4,7,10-,13,16, 19-heptazacyclotricos-21-yl]amino]butan-2-yl]amino]-3-hydroxy-1-oxo- butan-2-yl]amino]-1-oxobutan-2-yl]-6-methyloctanamide, or the sushi peptide comprises the amino acid sequence set forth in SEQ ID NO:1 .

3. The method of claim 1 wherein the poly(I:C) is high molecular weight poly(I:C).

4. The method of claim 1 wherein the subject is a human.

5. The method of claim 1 wherein the immune cells are T-cells or NK cells.

6. The method of claim 1 wherein, the whole blood comprises from about 80% to 100% by volume of the sample to be assayed.

7. The method of claim 1 wherein at least one of (i) the whole blood is collected in a tube comprising antigen, (ii) the whole blood is collected in a tube comprising heparin, or (iii) the whole blood is collected in a tube comprising a simple sugar in dried form.

8. The method of claim 1 wherein the at least one immune effector molecule is IFN-γ.

9. The method of claim 1 wherein in the step of measuring, the immune effector molecule is detected by ELISA.

* * * * *

UNITED STATES PATENT AND TRADEMARK OFFICE
CERTIFICATE OF CORRECTION

PATENT NO. : 10,578,612 B2
APPLICATION NO. : 13/700720
DATED : March 3, 2020
INVENTOR(S) : Anthony J. Radford et al.

It is certified that error appears in the above-identified patent and that said Letters Patent is hereby corrected as shown below:

In the Claims

Claim 2, Column 33, Lines 8-15:
"The method of claim 1 wherein the polymyxin B comprises N-[4-amino-1-[[1-[[4-amino-1-oxo-1-[[6,9,18-tris(2-aminoethyl)-15-benzyl-- 3-(1-hydroxyethyl)-12-(2-methylpropyl)-2,5,8,11,14,17,20-heptaoxo-1,4,7,10-,13,16,19-heptazacyclotricos-21-yl]amino]butan-2-yl]amino]-3-hydroxy-1-oxo-butan-2-yl]amino]-1-oxobutan-2-yl]-6-methyloctanamide, or the sushi peptide comprises the amino acid sequence set forth in SEQ ID NO:1." should read: --The method of claim 1 wherein the polymyxin B comprises N-[4-amino-1-[[1-[[4-amino-1-oxo-1-[[6,9,18-tris(2-aminoethyl)-15-benzyl-- 3-(1-hydroxyethyl)-12-(2-methylpropyl)-2,5,8,11,14,17,20-heptaoxo-1,4,7,10-,13,16,19-heptazacyclotricos-21-yl]amino]butan-2-yl]amino]-3-hydroxy-1-oxo-butan-2-yl]amino]-1-oxobutan-2-yl]-6-methyloctanamide, or the sushi peptide comprises the amino acid sequence set forth in SEQ ID NO:1.--

Claim 3, Column 33, Lines 16:
"The method of claim 1 wherein the polv(I:C) is high molecular weight poly(I:C)." should read: --The method of claim 1 wherein the poly(I:C) is high molecular weight poly(I:C).--

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*